United States Patent [19]
Dobson

[11] 3,975,364
[45] Aug. 17, 1976

[54] HALOGENATED ESTERS OF ALIPHATIC DICARBOXYLIC ACIDS

[75] Inventor: Kenneth Rowland Dobson, Epsom Downs, England

[73] Assignee: BP Chemicals International Limited, England

[22] Filed: Feb. 10, 1975

[21] Appl. No.: 548,557

Related U.S. Application Data

[63] Continuation-in-part of Ser. No. 387,951, Aug. 13, 1973, Pat. No. 3,890,375.

[30] Foreign Application Priority Data
Aug. 25, 1972 United Kingdom............... 39644/72

[52] U.S. Cl. ............................................. 260/485 H
[51] Int. Cl.$^2$.................... C07C 69/34; C07C 69/40
[58] Field of Search........................ 260/485 H, 633

[56] References Cited
UNITED STATES PATENTS
3,644,493   2/1972   Wygart et al. ................... 260/485 H Primary Examiner—Jane S. Myers

[57] ABSTRACT

The present invention relates to novel halogenated derivatives of esters of linear $C_8$ alcohols and aliphatic dicarboxylic acids and a process for the preparation of such compounds.

8 Claims, No Drawings

HALOGENATED ESTERS OF ALIPHATIC DICARBOXYLIC ACIDS

CROSS-REFERENCE TO RELATED APPLICATION

The present application is a continuation-in-part of my copending application Ser. No. 387,951, filed Aug. 13, 1973, now U.S. Pat. No. 3,890,375 entitled "Chemical Compound and Process", which is incorporated herein by reference thereto.

The present invention relates to novel halogenated derivatives of esters of linear $C_8$ alcohols.

Accordingly the present invention comprises esters of linear $C_8$ alcohols of the general formula:

(I)

or

(II)

wherein Z is $XCH_2.CHX$-,
and $Z^1$ is $-CHX.CHX$-,
and X is Cl or Br,
and R is a divalent saturated aliphatic radical or a direct bond, and Y is lower alkyl.O.CO-,

 

Preferably R is a direct bond or straight or branched chain divalent alkylene of 1 to 12, most preferably 1 to 6, carbon atoms. For example, R may be methylene, ethylene, propylene, butylene, hexylene, 1,2-butylene, etc.

Specific examples of the compounds of the invention include:
di(2,3,7,8-tetrachloro-1-octyl) succinate,
ethyl 2,3,7,8-tetrachloro-1-octyl succinate,
ethyl 1,2,7,8-tetrachloro-3-octyl succinate,
di(1,2,7,8-tetrachloro-3-octyl) succinate,
2,3,7,8-tetrachloro-1-octyl 1,2,7,8-tetrachloro-3-octyl succinate.

The carboxylic acid moiety in the ester group is derived from a saturated aliphatic dicarboxylic acid or a mono(lower alkyl)ester thereof.

According to a further aspect of the present invention, a process for preparing compounds of the formula (I) or (II) as hereinbefore defined comprises reacting in the liquid phase an octodienyl ester with halogen at ambient temperatures.

The term "halogen" as used here and throughout the specification means chlorine or bromine.

By the term "linear $C_8$ alcohols" it is meant throughout the specification that the carbon chain in the alcohol is linear. Thus the hydroxyl group of the alcohol could be in the 1- or 3-position of the carbon chain.

The term "lower alkyl" is meant throughout the specification a monovalent saturated straight or branched hydrocarbon chain of 1 to 6 carbon atoms.

The octodienyl ester may suitably be prepared by reacting in the liquid phase butadiene with a dicarboxylic acid, or a mono(lower alkyl) ester thereof, in the presence of a Group VIII metal catalyst as described in British Pat. Specification Ser. No. 1,274,072. The techniques used for this stage should be well known to a person skilled in the art.

The saturated aliphatic dicarboxylic acid or mono(lower alkyl) ester thereof may contain in addition inert substituents, e.g. halogens or alkyl groups, in the aliphatic chain thereof. Suitable examples of dicarboxylic acids and mono(lower alkyl) esters which may be used include oxalic acid, malonic acid, succinic acid, glutaric acid, adipic acid, octanedioic acid, decanedioic acid, dodecanedioic acid, etc., such acids substituted on one or more carbon atoms thereof by lower alkyl and/or halogens, and mono-(lower alkyl) esters thereof, such as methyl hydrogen malonate, ethyl hydrogen succinate, etc.

The product from the above esterification reaction is a mixture of 1- and 3-octadienyl diesters.

The mixture of 1- and 3-octadienyl esters thus obtained may be used for the halogenation step after separation from the catalyst solution by liquid/liquid extraction and removal of volatile olefins by distillation. The halogenation is carried out in the liquid phase by dissolving the octadienyl esters in a solvent. The solvents used for this purpose should preferably be more volatile than the esters and be inert to halogen, e.g. a halogenated hydrocarbon such as carbon tetrachloride or chloroform. Basic solvents such as pyridine may also be present. The appropriate halogen gas, e.g. chlorine, is then passed through the solution of the octadienyl esters.

The halogenation may be carried out in the dark and/or in the presence of a free radical inhibitor such as tertiary butyl catechol or oxygen. It may also be carried out in the presence of a Lewis acid such as ferric chloride.

The halogenation step may be carried out at ambient temperatures. By "ambient temperatures" is meant temperatures below 60°C, suitably below 40°C.

The halogenation step may be carried out at atmospheric, super-atmospheric or sub-atmospheric pressures.

The mixture of saturated halogenated derivatives thus obtained is then recovered by removal of the solvent and halogen by distillation under reduced pressure, or by liquid/liquid extraction, drying and removing the solvent by distillation. Where the dicarboxylic acid per se is employed as the reactant, the diester I or II will have as the Y group the residue of the linear $C_8$ alcohol. Where the mono(lower alkyl) ester form of the dicarboxylic acid is employed, the Y group of the diester I or II will be the lower alkyl of the dicarboxylic acid ester reactant.

The esters of linear $C_8$ alcohols described here may be used as plasticizers in polymeric material such as PVC, as components of lubricants and in heat exchange fluids.

The invention is further illustrated with reference to the following Example:

EXAMPLE

A mixture of ethyl 2,7-octadien-1-yl succinate (46g) and ethyl 1,7-octadien-3yl succinate (24g), prepared by reaction of butadiene with ethyl hydrogen succinic acid in the presence of a palladium catalyst, was dissolved in carbon tetrachloride (325ml). The solution was cooled below 0°C by means of an ice/salt bath and cooling coil, a slow stream of oxygen was passed through the solution, and the glass reaction vessel was covered with aluminum foil to exclude light. Chlorine gas was passed into the solution at such a rate that, with cooling, the temperature did not rise above 0°C. The end of the reaction was signalled by a drop in temperature of the reaction solution. The reaction solution was washed with aqueous sodium thiosulphate solution, sodium carbonate solution, water, and dried over magnesium sulphate. Removal of the carbon tetrachloride under reduced pressure gave a mixture of ethyl 2,3,7,8-tetrachloro-1-octyl succinate and ethyl 1,2,7,8-tetrachloro-3-octyl succinate as a colorless oil.

$C_{14}H_{22}O_4Cl_4$ requires: C, 42.4%; H, 5.5%; Cl, 35.9% MW (molecular weight) 396 found: C, 40.5%; H, 5.0%; Cl, 38.5%; MW, 492.

What is claimed is:

1. An ester of a linear $C_8$ alcohol of the general formula:

Z(CH$_2$)$_3$.Z$^1$.CH$_2$.O.CO.R.Y or

Z(CH$_2$)$_3$.CH(Z).O.CO.R.Y wherein

Z is XCH$_2$.CHX-,

Z$^1$ is -CHX.CHX-,

X is Cl or Br,

R is a divalent saturated aliphatic hydrocarbon radical which may be substituted by halogen or alkyl, or a direct bond, and Y is lower alkyl.O.CO-, Z(CH$_2$)$_3$.Z$^1$.CH$_2$.O.CH or Z(CH$_2$)$_3$.CH.O.CO.
                                            |
                                            Z 2. The compound of claim 1, wherein R is divalent straight or branched chain alkylene of 1-12 carbon atoms.

3. The compound of claim 1, wherein R is divalent straight or branched chain alkylene of 1-6 carbon atoms.

4. The compound of claim 1, wherein R is a direct bond.

5. The compound of claim 1, wherein Y is lower alkyl.O.CO.

6. The compound of claim 1, wherein Y is

Z(CH$_2$)$_3$.Z$^1$.CH$_2$.O.CO or Z(CH$_2$)$_3$.CH.O.CO.
                                            |
                                            Z

7. The compound of claim 1, which is ethyl 2,3,7,8-tetrachloro-1-octyl succinate.

8. The compound of claim 1, which is ethyl 1,2,7,8-tetrachloro-3-octyl succinate.

* * * * *